United States Patent [19]

Ishida et al.

[11] 4,088,646

[45] May 9, 1978

[54] 5-FLUOROURACIL DERIVATIVES

[75] Inventors: Torao Ishida; Daikichi Nishimura; Toshiaki Sugawara; Tadaaki Ooka, all of Fuji, Japan

[73] Assignee: Asahi Kasei Kogyo Kabushiki Kaisha, Osaka, Japan

[21] Appl. No.: 651,370

[22] Filed: Jan. 22, 1976

[30] Foreign Application Priority Data

Jan. 22, 1975 Japan .................................. 50-9469
Jan. 22, 1975 Japan .................................. 50-9470

[51] Int. Cl.² .......................................... C07D 239/22
[52] U.S. Cl. .................................... 544/313; 424/251
[58] Field of Search ........................................ 260/260

[56] References Cited

U.S. PATENT DOCUMENTS 2,949,451 8/1960 Hoffer .................................. 260/260
3,971,784 7/1976 Tada .................................... 260/260

Primary Examiner—Paul M. Coughlan, Jr.
Attorney, Agent, or Firm—Sughrue, Rothwell, Mion, Zinn and Macpeak

[57] ABSTRACT

A compound represented by the formulae:

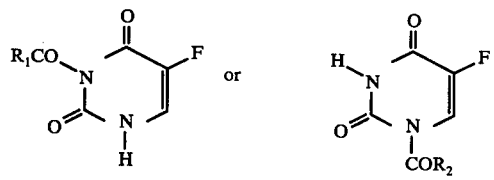

wherein $R_1$ and $R_2$ are as defined hereinafter, useful as an anti-cancer or anti-tumor agent.

3 Claims, 6 Drawing Figures

5-FLUOROURACIL DERIVATIVES

BACKGROUND OF THE INVENTION

1. Field of the Invention

This invention relates to novel 5-fluorouracil derivatives useful as an anti-cancer or anti-tumor agent. More particularly, this invention relates to 5-fluorouracil derivatives represented by the formulae:

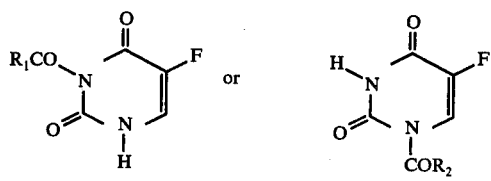

wherein $R_1$ represents an aryl group having 6 to 10 carbon atoms and $R_2$ represents an alkyl or alkenyl group having 9 to 23 carbon atoms.

2. Description of the Prior Art

5-Fluorouracil is a compound which inhibits the formation of nucleic acids in a living body by its metabolic antagonism, and, therefore, is useful as an anti-tumor agent. 5-Fluorouracil has been employed in the form of 1-N-substituted derivatives thereof, for example, the 1-N-tetrahydrofuranyl derivatives. However, the tetrahydrofuranyl group at the 1-N-substituent is a specific group and the industrial production thereof involves high costs. Other 1-N-substituted derivatives which have hitherto been proposed include 1-N-acetyl-5-fluorouracil (see U.S. Pat. No. 3,041,335), 1-N-benzoyl-5-fluorouracil (see Gann, 65, 463, 1974) and 1,3-di-N-benzoyl-5-fluorouracil (see West German Patent 2,455,423). However, 1-N-acetyl-5-fluorouracil is highly toxic, 1-N-benzoyl-5-fluorouracil cannot be synthesized on a reproducible basis, and 1,3-di-N-benzoyl-5-fluorouracil does not show reproducible activity.

SUMMARY OF THE INVENTION

The inventors conducted extensive investigations in order to develop novel compounds which can be produced on an industrial scale without the above described disadvantages associated with conventional 1-N-substituted-5-fluorouracils. As a result, the inventors found that uracil derivatives which have superior physiological activity to that of 1-N-tetrahydrofuranyl-5-fluorouracil and which are also of low toxicity can be obtained by using a higher aliphatic acyl group as a 1-N-substituent or an aromatic acyl group as a 3-N-substituent, thereby reaching the present invention.

The present invention, therefore, provides compounds represented by the formulae:

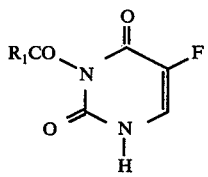

(I)

or

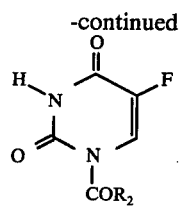

(II)

wherein $R_1$ represents an aryl group having 6 to 10 carbon atoms and $R_2$ represents an alkyl or alkenyl group having 9 to 23 carbon atoms, which possess superior physiological activity over that of 1-N-tetrahydrofuranyl-5-fluorouracil.

BRIEF EXPLANATION OF THE ACCOMPANYING DRAWINGS

FIGS. 1 to 6 show infrared absorption spectra of compounds according to the present invention.

DETAILED DESCRIPTION OF THE INVENTION

Figure 1:
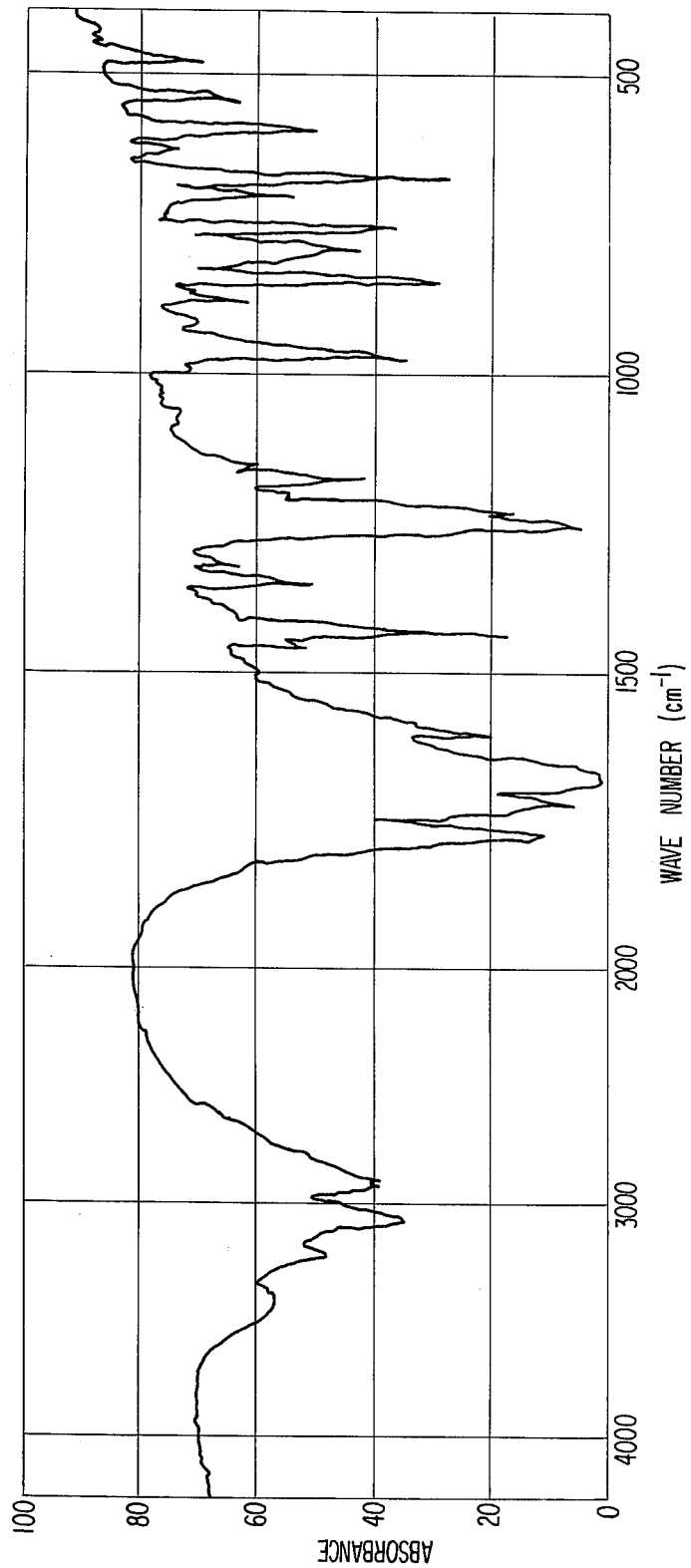

The term "aryl group having 6 to 10 carbon atoms" used for $R_1$ designates groups such as a phenyl, p-nitrophenyl, p-tolyl, p-methoxyphenyl and a p-n-butylphenyl group, preferably a phenyl group.

The term "alkyl group" used to define $R_2$ designates a straight or branched chain alkyl group having 9 to 23 carbon atoms such as a nonyl, decyl, undecyl, dodecyl, tridecyl, tetradecyl, pentadecyl, hexadecyl, heptadecyl, octadecyl, nonadecyl, eicosanyl, heneicosanyl, docosanyl and a tricosanyl group, preferably a pentadecyl, hexadecyl or heptadecyl group.

The term "alkenyl group" used to define $R_2$ designates a straight or branched chain alkenyl group having 9 to 23 carbon atoms such as a 7-nonenyl, 7-pentadecenyl, 9-heptadecenyl and a 9-tricosenyl group.

The 5-fluorouracil derivatives according to the present invention can be prepared by reacting 5-fluorouracil with an aromatic carboxylic acid halide represented by formula (III):

$$R_1COX \qquad (III)$$

wherein $R_1$ is as defined above and X represents a halogen atom such as a fluorine, chlorine, bromine or iodine atom. When the aromatic carboxylic acid halide is used in a relatively small amount, i.e., less than about 2 moles based on the 5-fluorouracil, a 3-N-acyl-5-fluorouracil represented by formula (I):

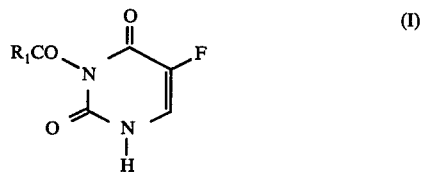

(I)

wherein $R_1$ is as defined above, is obtained. When the aromatic carboxylic acid halide is used in a large excess, i.e., in an amount of from about 3 to about 20 molar times the amount of the 5-fluorouracil, a known 1,3-di-N-acyl-5-fluorouracil of low activity is obtained.

Alternatively, the compounds of this invention can be prepared by reacting 5-fluorouracil with a reactive functional derivative of an organic acid represented by formula (IV):

$$R_2COOH \quad (IV)$$

wherein $R_2$ is as defined above. In this case, the resulting compound is a 1-N-acyl-5-fluorouracil represented by the following formula (II):

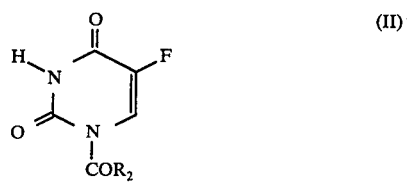

wherein $R_2$ is as defined above.

The acylating agent having formula (III) which can be used in this invention includes chlorides and bromides of an aromatic carboxylic acid such as benzoic acid, toluic acid, p-nitrobenzoic acid, anisic acid, p-n-butylbenzoic acid and the like. The acylating agent of formula (III) is used in an amount of about 1 to about 2 molar times the amount of 5-fluorouracil.

The reaction between 5-fluorouracil and the aromatic carboxylic acid halide of formula (III) is advantageously, but not mandatorily, carried out in a solvent in the presence of a base. Suitable solvents are non-polar solvents such as dioxane, benzene and the like. Preferred bases include organic bases such as pyridine, picoline, toluidine, triethylamine, dimethylaniline and the like. It is preferred to use these bases in an amount of from about 1 to about 20 molar equivalents with respect to the acylating agent employed, and the solvent in an amount of from about 1 to about 5 times the volume of the base used.

The above reaction is suitably carried out under 1 to 5 atmospheres pressure at a temperature from about 50 to about 150° C for a period of from about 0.5 to about 2 hours. After completion of the reaction, any unreacted reactants remaining in the reaction mixture are removed therefrom, whereafter the mixture can be purified, if necessary, by washing followed by either recrystallization from a solvent such as ethanol, isopropanol, benzene, ethyl acetate, hexane or the like, or chromatography using a silica gel column.

The organic acid represented by formula (IV) which can be used in this invention to introduce a substituent to the 1-N-position of 5-fluorouracil includes, for example, saturated aliphatic acids such as capric acid, n-undecanoic acid, lauric acid, n-tridecanoic acid, myristic acid, n-pentadecanoic acid, palmitic acid, margaric acid, stearic acid, n-nonadecanoic acid, arachidic acid, n-heneicosanoic acid, behenic acid, n-tricosanoic acid, lignoceric acid and the like, and unsaturated aliphatic acids such as decenoic acid, undecenoic acid, dodecenoic acid, tetradecenoic acid, hexadecenoic acid, octadecenoic acid, oleic acid, petroselinic acid, linolic acid, eicosenoic acid, eicosadienoic acid, erucic acid, docosadienoic acid and the like. These organic acids can be used in the form of a reactive functional derivative thereof, for example, in the form of an acid ester, an acid anhydride or an acid halide. It is preferable to use the functional derivative of the above described organic acid of formula (IV) in an amount of from about 1.5 to about 5 molar equivalents relative to 5-fluorouracil.

When the above organic acid is employed in the form of an acid anhydride or an acid halide as a reactive functional derivative, it is advantageous, but not mandatory, to carry out the reaction in a solvent in the presence of a base. Preferred bases are organic bases such as pyridine, picoline, toluidine, triethylamine, dimethylaniline and the like. Such a base is generally used in an amount of from about 2 to about 20 molar equivalents based on the acid anhydride or acid halide used. As a solvent, non-polar solvents such as dioxane, benzene and the like are most suitable. The solvent is suitably used in an amount of from about 1 to about 5 times the volume of the above described base.

The reaction between 5-fluorouracil and the reactive functional derivative of the compound of formula (IV) can generally be carried out under 1 to 5 atmospheres pressure at a temperature ranging from about 50° to about 150° C for a period of from about 0.5 to about 2 hours. After the solvent is removed, the reaction mixture can be washed with hexane, benzene, acetone or a like solvent to remove most of the organic acid and unreacted reactants, if necessary, whereafter the residue is purified by recrystallization from an appropriate solvent, such as benzene, toluene, ethyl acetate, diethyl ether, hexane and the like.

The structure of the compounds according to the present invention as illustrated by chemical formulae (I) or (II) can be determined by the chemical shift of the nuclear magnetic resonance spectrum of the 6-position proton ($H_6$). That is, the 5-fluorouracil is capable of being acylated either at the 1-N-position or the 3-N-position. The chemical shift of $H_6$ of 5-fluorouracil in pyridine-$d_5$ is $\delta 7.74$ ppm, and when the 5-fluorouracil is acylated, the $H_6$ shifts to the lower magnetic field. The chemical shift of $H_6$ of the known 1,3-di-N-benzoyl-5-fluorouracil, i.e., the compound having the 1-N-position acylated, is in the vicinity of $\delta 8.75$ ppm, and that of any of the compounds having formula (II) is in the vicinity of $\delta 8.46$ to 8.47 ppm. On the other hand, the chemical shift of $H_6$ of the compounds having formula (I) obtained in this invention is $\delta 8.04$ ppm. Since it is believed that the shift of $H_6$ to the lower magnetic field is greater in the case where the acylation is effected at the 1-N-position than the case wherein the acylation takes place at the 3-N-position, it can be confirmed that acylation took place at the 1-N-position with the compounds of formula (I) and at the 3-N-position with the compounds of formula (II), respectively.

As previously described, the compounds obtained according to the present invention are useful as an anti-cancer or anti-tumor agent.

The present invention will now be illustrated in greater detail by way of the several Examples hereinafter given of presently preferred embodiments of the invention, but it should be understood that these Examples are given for illustrative purposes only and are not to be construed as limiting the present invention. In the Examples, all parts, percentages, ratios and the like are by weight and all processings were at atmospheric pressure, unless otherwise indicated.

EXAMPLE 1

2.6 g (0.02 mole) of 5-fluorouracil was suspended in 10 ml of absolute pyridine and 10 ml of absolute dioxane, and the suspension was warmed to 80° C and stirred. 5.6 g (0.04 mole) of benzoyl chloride was then added dropwise thereto followed by stirring at 80° C for 1.5 hours to allow the mixture to react. After completion of the reaction, the reaction mixture was poured into ice-water followed by stirring, and the thus precipitated solid was filtered, washed with water and then dissolved in benzene while hot (80° C). Any insoluble matter was removed by filtration, and the filtrate allowed to cool to precipitate crystals, which were recovered by filtration to obtain 1.5 g of 3-N-benzoyl-5-fluorouracil in a yield of 32% (the filtrate was set aside). Melting Point: 170° C.

Elementary Analysis for $C_{11}H_7FN_2O_3$:Calcd. (%): C, 56.42; H, 3.01; N 11.96. Found (%): C, 56.59; H, 3.10; N 11.75.

Ultraviolet Absorption Spectrum (UV): $\lambda_{max}$ 254 mμ (methanol).

Nuclear Magnetic Resonance Spectrum (NMR): (pyridine-$d_5$) $\delta 8.04$ (d, 1, $J_{5-6}$ = 6.0 Hz, $H_6$), $\delta 8.12$ (2, benzene ring proton) and $\delta 7.30 - 7.52$ (3, benzene ring proton).

The infrared absorption spectrum (IR) of the above product is shown in FIG. 1.

The above filtrate was concentrated under reduced pressure (25 mm Hg), and the residue washed three times using 10 ml portions of hot hexane (50° C) and dissolved in ethanol. Hexane was added to the resulting solution until the mixture just became turbid followed by allowing the mixture to cool to precipitate crystals, which were then filtered to obtain 0.2 g of 1,3-di-N-benzoyl-5-fluorouracil in a yield of 3%. Melting Point: 195° C.

Elementary Analysis for $C_{18}H_{11}FN_2O_3$:Calcd. (%): C, 63.90; H, 3.28; N, 8.28. Found (%): C, 63.61; H, 3.53; N, 8.45.

UV Spectrum: $\lambda_{max}$ 281mμ, 242 mμ (methanol).

NMR Spectrum: (pyridine-$d_5$) $\delta 8.75$ (d, 1, $J_{5-6}$ = 7.0 Hz, $H_6$) $\delta 8.10 - 8.40$ (4, benzene ring proton) and $\delta 7.30 - 7.60$ (6, benzene ring proton).

Figure 2:
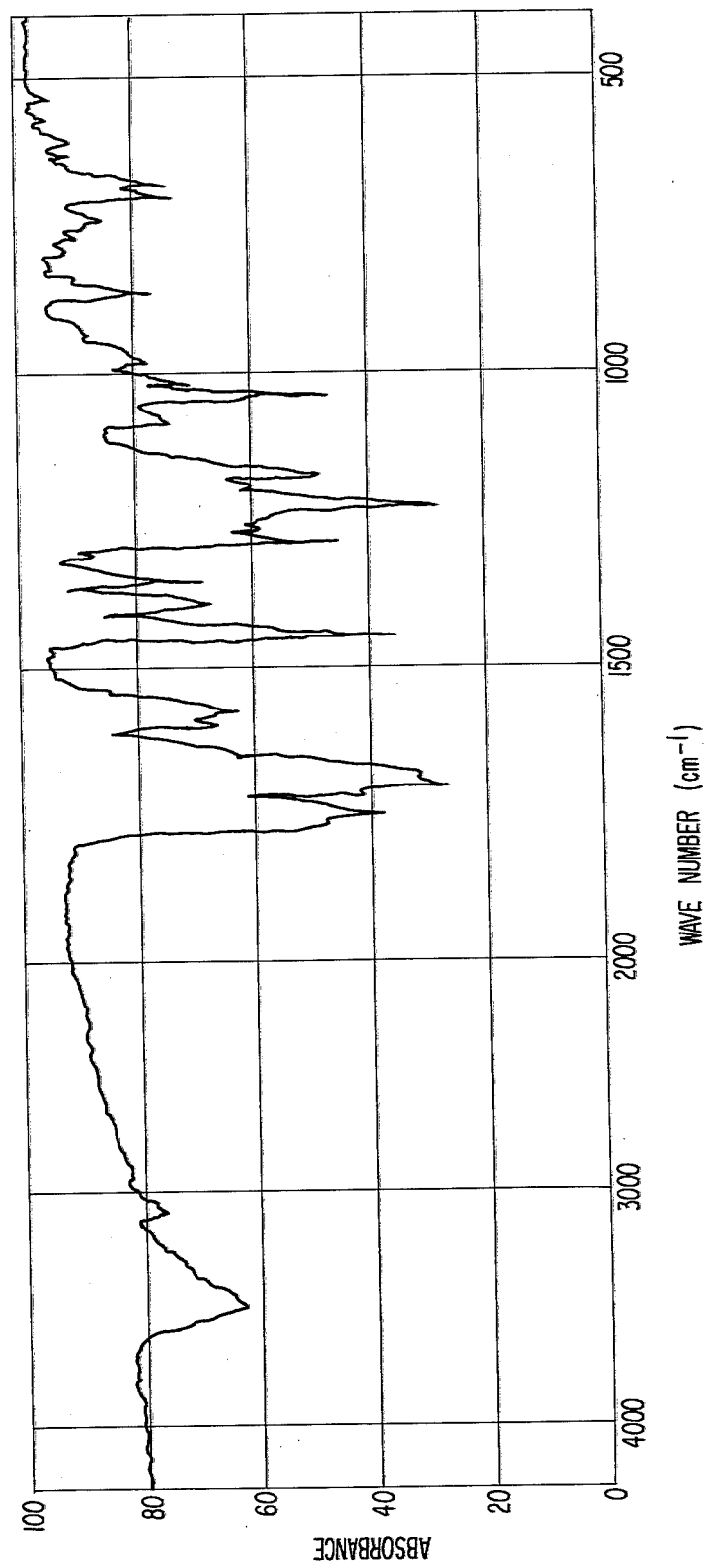

The IR spectrum of the product is shown in FIG. 2.

EXAMPLE 2

2.6 g (0.02 mole) of 5-fluorouracil was suspended in 10 ml of absolute pyridine, and the suspension was stirred at 70° C to form a solution. 17 g (0.12 mole) of benzoyl chloride was added dropwise to the resulting solution followed by heating to 80° C for 1.5 hours while stirring. After completion of the reaction, the reaction mixture was concentrated under reduced pressure (25 mm Hg) to half its original volume, and 50 ml of ethyl acetate was added thereto. After the insoluble matter in the ethyl acetate was removed, the solution was washed twice with water, and dried over Glauber's salt, and the ethyl acetate removed therefrom under reduced pressure (25 mm Hg). Ethanol was then added to the residue, and the mixture heated to 80° C to form a solution followed by allowing the resulting solution to cool to precipitate crystals, which were then filtered to obtain 3.4 g of 1,3-di-N-benzoyl-5-fluorouracil in a yield of 51%.

The filtrate obtained after the recovery of the above product was concentrated under reduced pressure (25 mm Hg), and the resulting residue separated and purified by chromatography using a silica gel column and ethyl acetate as an eluent. Recrystallization of the product from benzene gave 1.1 g of 3-N-benzoyl-5-fluorouracil in a yield of 24%.

The 3-N-benzoyl-5-fluorouracil and the 1,3-di-N-benzoyl-5-fluorouracil as above obtained were confirmed to be consistent with the respective samples obtained in Example 1 based on the melting point, IR spectrum and NMR spectrum thereof.

EXAMPLE 3

In the same manner as described in Example 1 but using 2.6 g (0.02 mole) of 5-fluorouracil, 10 ml of absolute pyridine and 7.4 g (0.04 mole) of benzoyl bromide, 1.6 g of 3-N-benzoyl-5-fluorouracil (yield, 34%) and 270 mg of 1,3-di-N-benzoyl-5-fluorouracil (yield, 4%) were obtained.

EXAMPLE 4

In the same manner as described in Example 1, the reaction was carried out using 2.6 g (0.02 mole) of 5-fluorouracil, 10 ml of absolute pyridine, 10 ml of absolute dioxane and 7.4 g (0.04 mole) of p-nitrobenzoyl chloride to obtain 1.8 g of 3-N-(p-nitrobenzoyl)-5-fluorouracil (yield, 32%) and 0.25 g of 1,3-di-N-(p-nitrobenzoyl)-5-fluorouracil (yield, 3%).

EXAMPLE 5

2.6 g of 5-fluorouracil was suspended in 20 ml of absolute pyridine, and 20 g of stearic anhydride was added to the resulting suspension. The mixture was heated at 100° C for 1 hour with stirring. After the reaction was completed, pyridine was removed under reduced pressure (25 mm Hg), and the residual solid was dissolved in benzene followed by allowing the solution to cool. The precipitated crystals were filtered, washed with hot hexane and recrystallized from benzene to obtain 5.5 g of 1-N-stearoyl-5-fluorouracil in a yield of 69%. Melting Point: 101° C.

Elementary Analysis for $C_{22}H_{37}FN_2O_3$:Calcd. (%): C, 66.62; H, 9.42; N, 7.06. Found (%): C, 66.51; H, 9.65; N, 7.28.

UV Spectrum: $\lambda_{max}$ 261 mμ (dioxane).

NMR Spectrum (pyridine-$d_5$): $\delta 8.47$ (d, 1, $J_{5-6}$ = 8.0 Hz, $H_6$), $\delta 3.30$ (t, 2, $-COCH_2-$), $\delta 1.20 - 2.00$ (30, $CH_2 \times 15$) and $\delta 0.88$ (t, 3, terminal $CH_3$).

Figure 3:
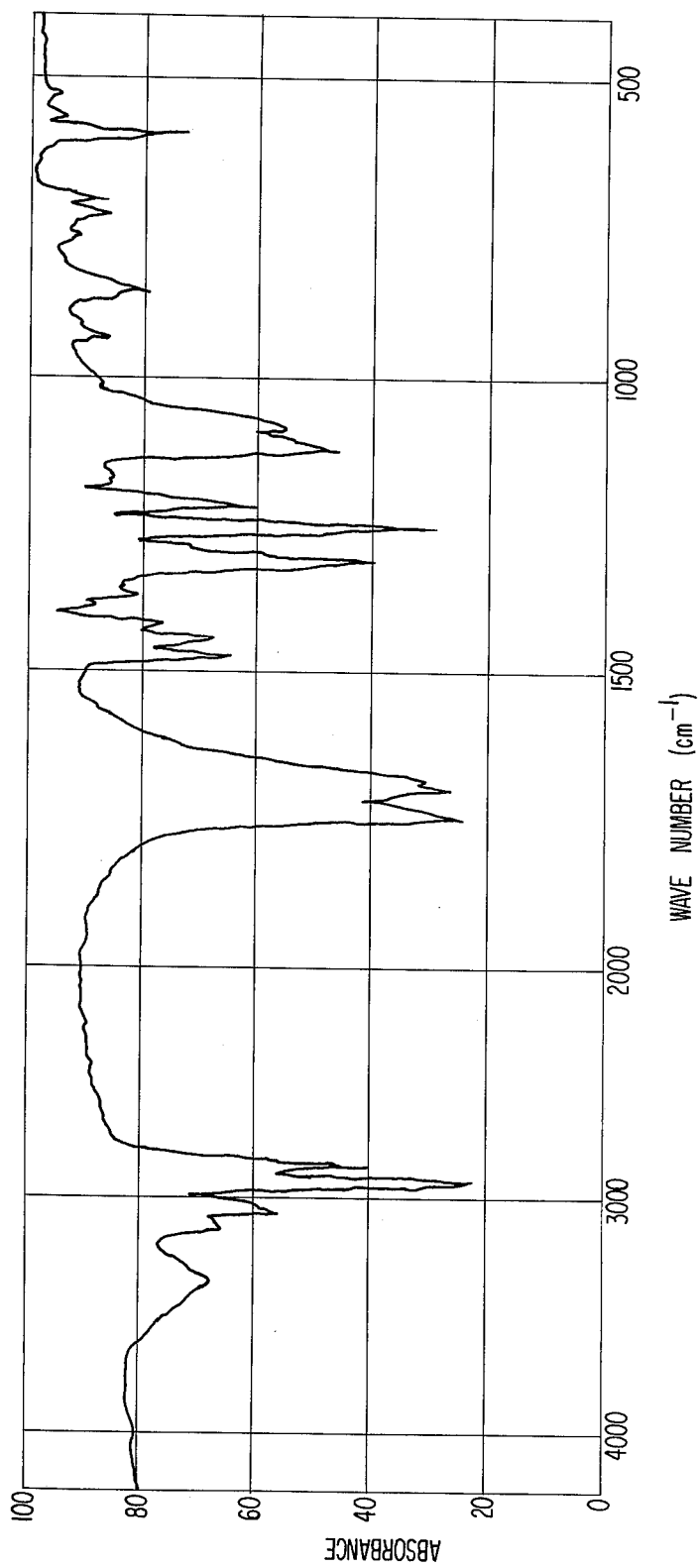

The IR spectrum of the product is shown in FIG. 3.

EXAMPLE 6

2.6 g of 5-fluorouracil was suspended in 20 ml of absolute dioxane and 10 ml of absolute pyridine, and 20 g of margaric anhydride was added thereto followed by heating at 80° C for 1 hour with stirring. After the reaction was completed, the solvent was removed under reduced pressure (25 mm Hg), and the residual solid was washed with hot hexane (50° C). Any insoluble matter in the hot hexane was recrystallized from benzene to obtain 5.0 g of 1-N-margaroyl-5-fluorouracil in a yield of 65%. Melting Point: 102° C.

Elementary Analysis for $C_{21}H_{35}FN_2O_3$:Calcd. (%): C, 65.92; H, 9.24; N, 7.32. Found (%): C, 65.71; H, 9.45; N, 7.47.

UV Spectrum: $\lambda_{max}$ 262 mμ (dioxane).

NMR Spectrum (pyridine-$d_5$): $\delta 8.46$ (d, 1, $J_{5-6}$ = 8.0 Hz, $H_6$), $\delta 3.28$ (t, 2, $-COCH_2-$), $\delta 1.20 - 2.00$ (28, $CH_2 \times 14$) and $\delta 0.86$ (t, 3, terminal $CH_3$).

Figure 4:
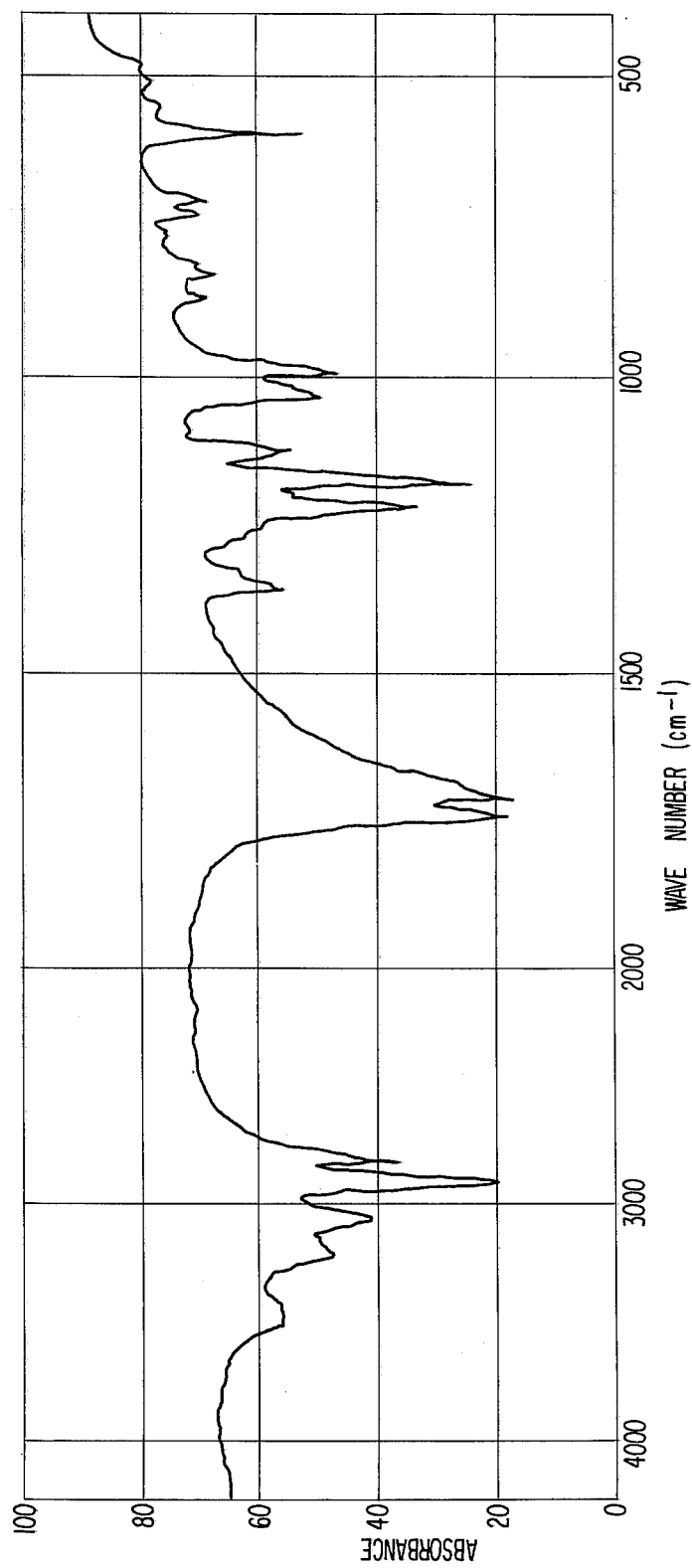

The IR spectrum of the product is shown in FIG. 4.

EXAMPLE 7

2.6 g of 5-fluorouracil was suspended in 20 ml of absolute dioxane and 10 ml of absolute pyridine, and 15 g of palmityl chloride was added to the suspension followed by heating at 80° C for 1 hour while stirring. After completion of the reaction, the solvent was removed under reduced pressure (25 mm Hg), and the residual solid was washed with hot hexane (50° C). Any insoluble matter in the hot hexane was recrystallized from benzene to obtain 4.0 g of 1-N-palmitoyl-5-fluorouracil in a yield of 54%. Melting Point: 98° C.

Elementary Analysis for $C_{20}H_{33}FN_2O_3$:Calcd. (%): C, 65.17; H, 9.04; N, 7.60. Found (%): C, 65.42; H, 9.17; N, 7.53.

UV Spectrum: $\lambda_{max}$ 261 m$\mu$ (dioxane).

NMR Spectrum (pyridine-$d_5$): $\delta$8.46 (d, 1, $J_{5-6}$ = 8.0 Hz, $H_6$), $\delta$3.28 (t, 2, —$COCH_2$—), $\delta$1.20 – 2.00 (26, $CH_2$ × 13) and $\delta$0.84 (t, 3, terminal $CH_3$).

Figure 5:
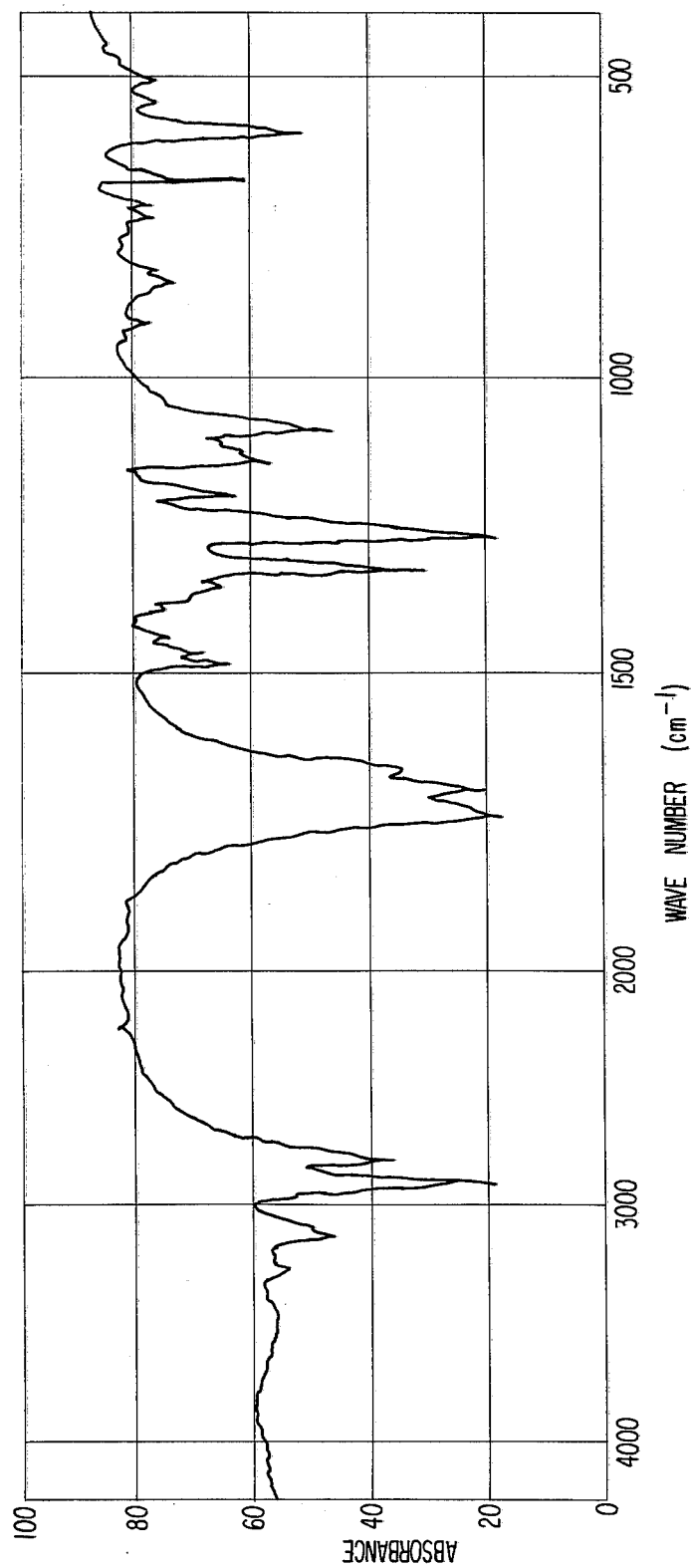

The IR spectrum of the product is shown in FIG. 5.

EXAMPLE 8

2.3 g of 3-N-benzoyl-5-fluorouracil was suspended in 20 ml of absolute dioxane and 5 ml of absolute pyridine, and 10 g of stearic anhydride was added to the suspension followed by heating at 80° C for 1 hour with stirring. After completion of the reaction, the solvent was removed under reduced pressure (25 mm Hg), and the residual solid was dissolved in acetone. After the insoluble matter was removed, the solution was cooled in a refrigerator to 0° to −4° C. The precipitated stearic acid and the unreacted stearic anhydride were filtered, and the filtrate was concentrated under reduced pressure (25 mm Hg). Repeated crystallizations, of the residue from hexane gave 2 g of 3-N-benzoyl-1-N-stearoyl-5-fluorouracil in a yield of 40%. Melting Point: 85° C.

Elementary Analysis for $C_{29}H_{41}FN_2O_4$:Calcd. (%): C, 69.56; H, 8.27; N, 5.60. Found (%): C, 69.74; H, 8.51; N, 5.48.

UV Spectrum: $\lambda_{max}$ 255 m$\mu$ (diethyl ether).

NMR Spectrum (pyridine-$d_5$): $\delta$8.75 (d, 1, $J_{5-6}$ = 7.0 Hz, $H_6$), $\delta$8.26 (2, benzene ring proton), $\delta$7.2 – 7.6 (3, benzene ring proton), $\delta$3.12 (t, 2,—$COCH_2$—), $\delta$1.20 – 2.00 (30, $CH_2$ × 15) and $\delta$0.84 (3, terminal $CH_3$).

Figure 6:
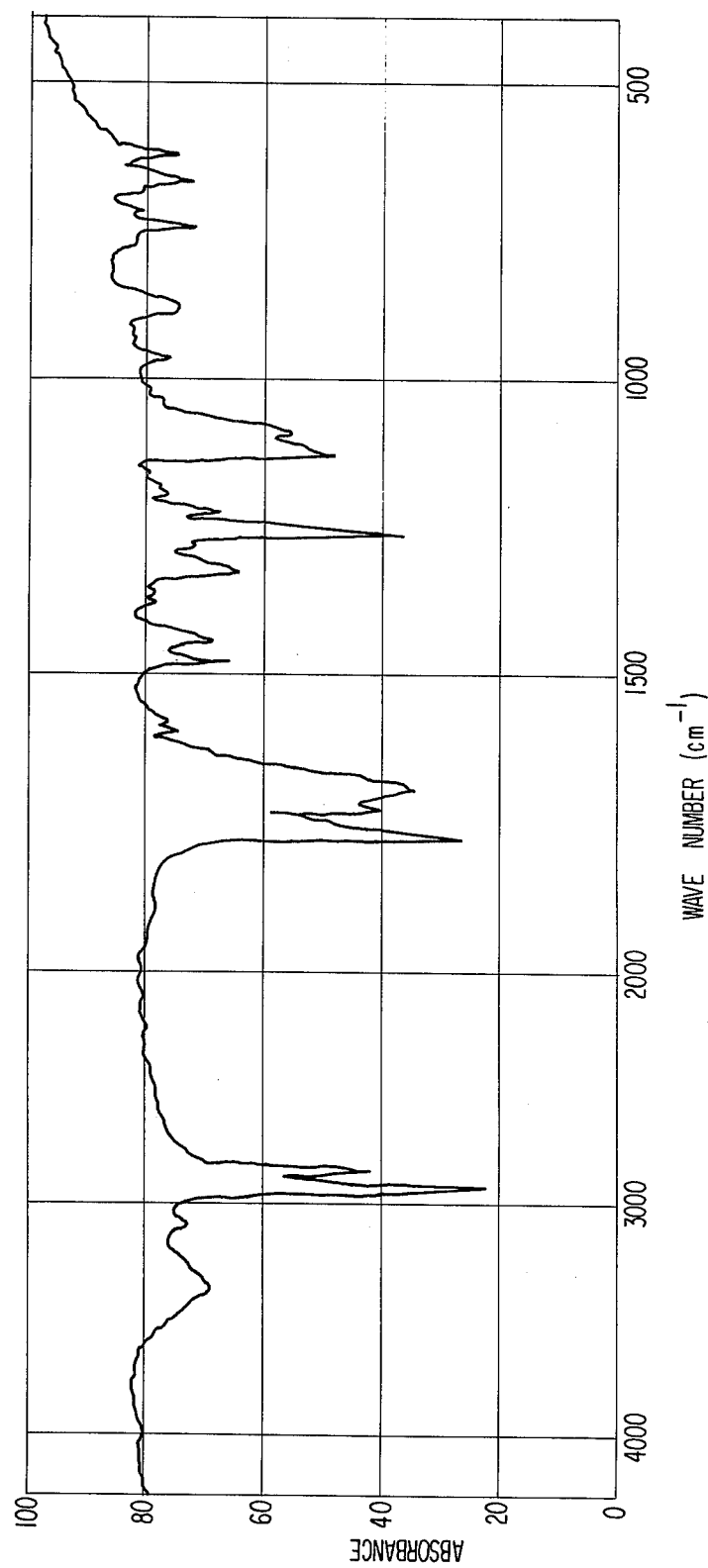

The IR spectrum of the product is shown in FIG. 6.

The anti-cancer activity of the compounds according to this invention against L1210, one type of cancer encountered in mice, was compared with that of a commercially available anti-cancer agent, 1-N-tetrahydrofuranyl-5-fluorouracil. As a result, it was found that the compounds of this invention exhibited superior anti-cancer effects against L1210 as compared to those of 1-N-tetrahydrofuranyl-5-fluorouracil as shown in the following Biological Experimentation Example.

BIOLOGICAL EXPERIMENTATION EXAMPLE

1 × 10$^5$ cells of L1210 were intraperitionally transplanted to mice ($CDF_1$, 10 mice per group). 24 hours after the transplant, the test compound as indicated in the Table below (10 to 100 mg of the test compound was suspended in 1 ml of a physiological saline solution and 0.05 ml of Tween-80 (trade name of a nonionic surface active agent, manufactured by Atlas Powder Co., U.S.A.) was added thereto) was administered to each mouse at a single dose level of 10 to 100 mg/kg body weight per day for a period of 5 days. As a control, a mixture of Tween-80 and a physiological saline solution containing no test compound was administered.

The anti-cancer effects of the test compounds are shown in the Table below in terms of the percentage of the average survival days in test groups (T) to the average survival days in a control group (C) (T/C %). Therefore, a T/C % less than 100% indicates the test compound was toxic whereas a T/C % higher than 100% indicates that the compound possessed an anti-cancer effect.

TABLE

| Test Compound | Dose Level (mg/kg/day) | T/C (%) |
|---|---|---|
| 3-N-benzoyl-5-fluorouracil | 100 | 100 |
|  | 75 | 130 |
|  | 50 | 180 |
|  | 25 | 160 |
| 1-N-stearoyl-5-fluorouracil | 100 | 110 |
|  | 75 | 150 |
|  | 50 | 200 |
|  | 25 | 170 |
| 1-N-margaroyl-5-fluorouracil | 100 | 100 |
|  | 75 | 140 |
|  | 50 | 190 |
|  | 25 | 170 |
| 1-N-palmitoyl-5-fluorouracil | 100 | 100 |
|  | 75 | 130 |
|  | 50 | 190 |
|  | 25 | 150 |
| 3-N-benzoyl-1-N-stearoyl-5-fluorouracil | 100 | 110 |
|  | 75 | 100 |
|  | 50 | 100 |
|  | 25 | 100 |
| 1-N-tetrahydrofuranyl-5-fluorouracil | 100 | 140 |
|  | 75 | 100 |
|  | 50 | 100 |
|  | 25 | 100 |

While the invention has been described in detail and with reference to specific embodiments thereof, it will be apparent to one skilled in the art that various changes and modifications can be made therein without departing from the spirit and scope thereof.

What is claimed is:

1. A compound represented by the formula:

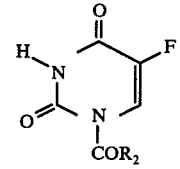

wherein $R_2$ represents alkyl or alkenyl having 9 to 23 carbon atoms.

2. The compound as claimed in claim 1, wherein $R_2$ is nonyl, decyl, undecyl, dodecyl, tridecyl, tetradecyl, pentadecyl, hexadecyl, heptadecyl, octadecyl, nonadecyl, eicosanyl, heneicosanyl, docosanyl or tricosanyl.

3. The compound as claimed in claim 1, wherein $R_2$ is pentadecyl, hexadecyl or heptadecyl.

* * * * *